United States Patent
Trieu et al.

(10) Patent No.: US 8,268,010 B2
(45) Date of Patent: Sep. 18, 2012

(54) SYSTEM AND METHOD FOR FORMING BONE FILLING MATERIALS WITH MICROPARTICLES

(75) Inventors: Hai H. Trieu, Cordova, TN (US);
Aashiish Agnihotri, Memphis, TN (US);
Joseph Saladino, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1418 days.

(21) Appl. No.: 11/622,547

(22) Filed: Jan. 12, 2007

(65) Prior Publication Data
US 2008/0172131 A1 Jul. 17, 2008

(51) Int. Cl.
*A61F 2/44* (2006.01)
*A61F 2/02* (2006.01)

(52) U.S. Cl. .................. 623/23.73; 623/17.11

(58) Field of Classification Search ............... 606/86 R; 623/17.11–17.16, 23.73
See application file for complete search history.

(56) References Cited

U.S. PATENT DOCUMENTS

| | | | |
|---|---|---|---|
| 5,047,031 A | 9/1991 | Constantz | |
| 5,525,148 A | 6/1996 | Chow et al. | |
| 5,650,108 A | 7/1997 | Nies et al. | |
| 5,695,678 A * | 12/1997 | Edamura et al. | 252/74 |
| 5,795,922 A * | 8/1998 | Demian et al. | 523/117 |
| 5,820,632 A | 10/1998 | Constantz et al. | |
| 6,083,264 A | 7/2000 | Wood et al. | |
| 6,479,565 B1 | 11/2002 | Stanley | |
| 6,547,866 B1 | 4/2003 | Edwards et al. | |
| 6,726,691 B2 * | 4/2004 | Osorio et al. | 606/94 |
| 2005/0059979 A1 * | 3/2005 | Yetkinler et al. | 606/92 |
| 2005/0197422 A1 | 9/2005 | Mayadunne et al. | |
| 2006/0074424 A1 * | 4/2006 | Alleyne et al. | 606/76 |
| 2006/0095138 A1 * | 5/2006 | Truckai et al. | 623/23.62 |
| 2006/0122614 A1 * | 6/2006 | Truckai et al. | 606/76 |
| 2006/0122625 A1 * | 6/2006 | Truckai et al. | 606/94 |
| 2006/0195115 A1 * | 8/2006 | Ferree | 606/92 |
| 2006/0233851 A1 * | 10/2006 | Simon et al. | 424/422 |
| 2007/0191963 A1 * | 8/2007 | Winterbottom et al. | 623/23.5 |
| 2007/0213717 A1 * | 9/2007 | Trieu et al. | 606/61 |
| 2007/0213718 A1 * | 9/2007 | Trieu | 606/61 |
| 2007/0213822 A1 * | 9/2007 | Trieu | 623/17.11 |
| 2007/0213823 A1 * | 9/2007 | Trieu | 623/17.11 |
| 2007/0213824 A1 * | 9/2007 | Trieu | 623/17.11 |
| 2008/0103564 A1 * | 5/2008 | Burkinshaw et al. | 607/96 |

OTHER PUBLICATIONS

Iooss et al., A new injectable bone substitute combining poly microparticles with biphasic calcium phospate granules. Biomaterials 22 (2001) 2785-2794.*
Ioosi P et al.: "A new injectable bone substitute combining poly(e-caprolactone) microparticles with bisphasic calcium phosphate granules", Biomaterials, Elsevier Science Publishers BV., Barking, GB, vol. 22, No. 20, Oct. 15, 2001, pp. 2785-2794, XP004297229, ISSN: 0142-9612 abstract.
International Search Report for Application No. PCT/US2008/050957 mailed Apr. 23, 2009.

(Continued)

*Primary Examiner* — Kevin T Truong
*Assistant Examiner* — David Bates

(57) ABSTRACT

A method for treating a vertebral bone comprises providing a plurality of hollow microparticles and providing a flowable and settable bone filling material. The method further comprises mixing the plurality of hollow microparticles with the bone filling material to form a bone augmentation material. The method further comprises inserting an injection device into the vertebral bone and injecting the bone augmentation material from the injection device and into the vertebral bone.

17 Claims, 3 Drawing Sheets

OTHER PUBLICATIONS

A. Boger, S. Verrier, M. Bohner, P. Heini, E. Schneider; Properties of an injectable low modulus PMMA bone cement for vertebroplasty; European Cells and Materials vol. 10. Suppl. 1, 2005 (p. 17); AO Research Institute, Davos, Switzerland.

A. Boger, P. Heini, M. Bohner, E. Schneider; Vertebral Cancellous Bone Augmented with Stiffness-adapted PMMA Cement does not Show Acute Failure under Dynamic Loading; European Cells and Materials vol. 11. Suppl. 1, 2006 (p. 29); AO Research Institute, Davos, Switzerland.

U.S. Appl. No. 11/622,570, filed Jan. 12, 2007 in the name of Trieu, et al.

U.S. Appl. No. 11/622,558, filed Jan. 12, 2007 in the name of Trieu, et al.

* cited by examiner

SYSTEM AND METHOD FOR FORMING BONE FILLING MATERIALS WITH MICROPARTICLES

CROSS REFERENCE

The related applications, incorporated by reference herein, are:

U.S. Utility patent application Ser. No. 11/622,558, filed on Jan. 12, 2007 and entitled "System and Method for Pressure Mixing Bone Filling Materials" and U.S. Utility patent application Ser. No. 11/622,570, filed on Jan. 12, 2007 and entitled "System and Method for Forming Porous Bone Filling Materials.

BACKGROUND

Bone cements and other bone filling materials are currently used throughout the skeletal system to augment or replace bone weakened or lost to disease or injury. One example of a treatment that includes the administration of bone filling material is vertebroplasty. During vertebroplasty, the cancellous bone of a vertebral body is supplemented with bone filling material. Frequently, the available bone filling materials do not possess material properties similar to the native bone. Materials, systems, and methods are needed to form and deliver bone filling materials that may be selectively matched to the natural bone undergoing treatment.

SUMMARY

In one embodiment, a method for treating a vertebral bone comprises providing a plurality of hollow microparticles and providing a flowable and settable bone filling material. The method further comprises mixing the plurality of hollow microparticles with the bone filling material to form a bone augmentation material. The method further comprises inserting an injection device into the vertebral bone and injecting the bone augmentation material from the injection device and into the vertebral bone.

In another embodiment, a bone augmentation system comprises a plurality of hollow microparticles wherein each of the plurality of hollow particles has a outer shell, formed of a polymer or a metal. The bone augmentation system further comprises a flowable and settable bone filling material. An injection instrument comprises a reservoir region for containing a mixture of the flowable and settable bone filling material and the plurality of hollow microparticles. The injection instrument also comprises a dispensing device configured to move into the reservoir region to deliver the mixture into a body region adjacent cancellous bone.

In another embodiment, a bone augmentation material for injection into a cancellous bone region comprises a plurality of hollow microspheres with each microsphere comprising a polymeric shell. The bone augmentation material further comprises a bone filling medium. The bone augmentation material has a first stage in which the plurality of hollow microspheres are movable within the bone filling medium and a second stage in which the plurality of microspheres are suspended and immovable within the bone filling medium.

Additional embodiments are included in the attached drawings and the description provided below.

DETAILED DESCRIPTION

Figure 1:
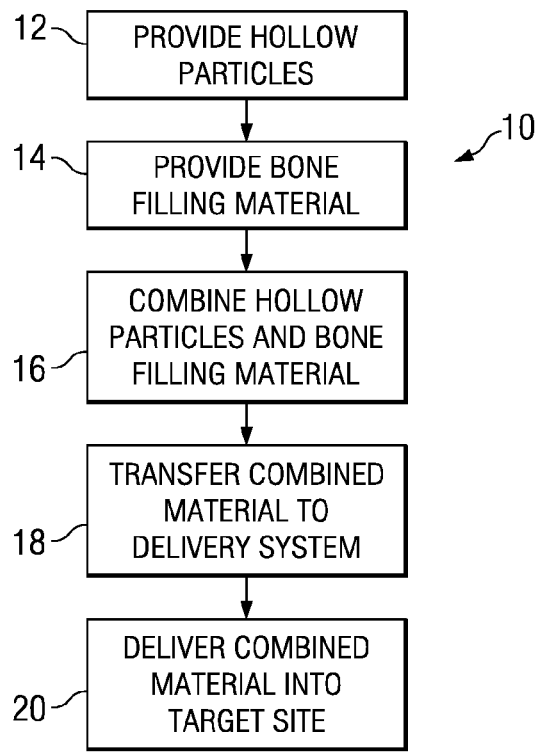
FIG. 1 is a flowchart for a process of forming a modulated bone filling material according to one embodiment of the disclosure.

The present disclosure relates generally to devices, methods and apparatus for augmenting bone, and more particularly, to methods and instruments for augmenting bone with a bone augmentation material comprising microparticles. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a method for forming a modified or modulated bone augmentation material that may better correspond to the material characteristics, including the modulus of elasticity, of a target bone region as compared to unmodulated bone cement. At step 12, a quantity of microparticles are selected to modulate the material properties of a bone filling material such as bone cement. The selected microparticles may be of the same size or have varying sizes. Likewise, the selected microparticles may have the same material properties or have varying material properties. The selected microparticles may be provided in any suitable three dimensional shape including spheres, ellipsoids, cubes, pyramids, or other irregular shapes.

Figure 2:
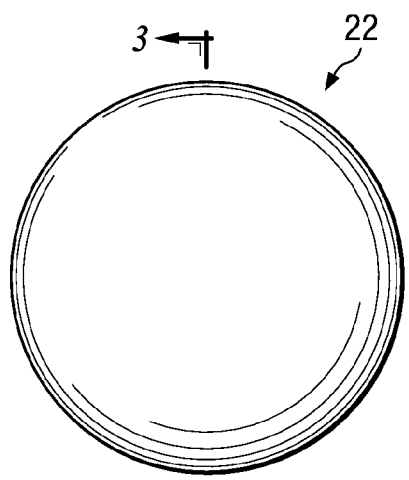
FIG. 2 is a front elevation view of a microparticle according to one embodiment of the present disclosure.
Figure 3:
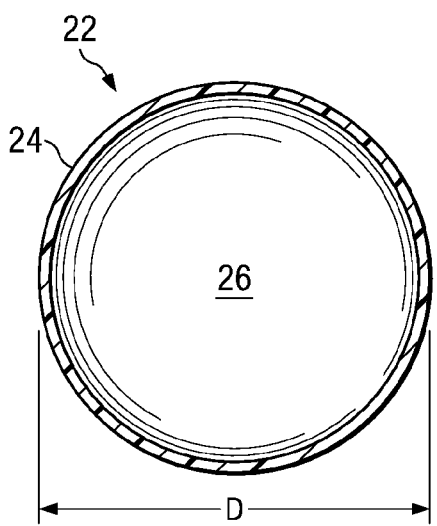
FIG. 3 is a cross sectional view of the microparticle of FIG. 2.

Referring now to FIGS. 2-3, in one embodiment a microparticle 22 is a generally hollow sphere and includes and outer shell 24 surrounding an inner region 26. The outer shell may be formed of any of a variety of materials including polymers, ceramics, or metals. Suitable polymers may include polymethylmethacrylate (PMMA), acrylate polymers, silicone, nylon, or polyurethanes. Suitable ceramics may include calcium phosphate, alumina, silica or pyrolytic carbon. Suitable metals may include cobalt-chromium alloys, titanium alloys, nickel titanium alloys, NITINOL, or stainless steel alloys. The outer shell may be a uniform material or may be formed of interwoven materials. Further, the outer shell may be molded, blown, braided, knit or otherwise formed to maintain a open inner region. The inner region 26 may be completely void of material or may be filled such as with air, saline, silicon, or other fluid or viscous materials. The outer shell may be formed of biostable or biodegradable material. A biodegradable material may be selected that would degrade during or after the hardening of the bone augmentation material, creating a porous mass that promotes bone ingrowth and releasing any additives that may have been included in the inner region.

In the embodiment of FIGS. 2-3, the microsphere 22 may have a diameter D between 100 and 300 microns (μm). Other suitable microsphere diameters may range from 1 to 2000 microns, with diameters in the range of 10-500 microns being particularly suitable to many applications. The quantity of selected microparticles may be dependent upon the size, density, and material properties of the microparticles. For example, highly deformable microparticles may impart the modulated bone augmentation material with a lower modulus of elasticity than would less flexible microparticles of the same size. Further, larger microparticles may impart a lower modulus than the same quantity of smaller microparticles of the same material. A higher density of microparticles may impart a lower modulus to the bone augmentation material than would a less dense array of microparticles of the same size and material properties.

The quantity of selected microparticles may also be dependent upon the size of the target bone region and characteristics of the patient including the age, bone density, body mass index, or health of the patient. For example, an elderly osteoporotic vertebroplasty patient may require a more reduced modulus bone augmentation material than would a young healthy trauma victim undergoing a similar procedure.

Referring again to FIG. 1, at step 14, an appropriate bone filling material may be selected. Suitable bone filling materials may include polymethylmethacrylate (PMMA) bone cement, calcium phosphate bone cement, calcium sulfate compounds, calcium aluminate compounds, aluminum silicate compounds, hydroxyapatite compounds, in situ curable ceramics or polymers, or other flowable materials that become more rigid after delivery. The bone filling material may be provided as multiple components such as, a PMMA powder and a PMMA monomer. Generally, the bone filling material may have a higher modulus of elasticity in a final hardened or cured state than does the selected quantity of microparticles, so that adding the microparticles may have the effect of reducing the overall modulus of the combined material. In FIG. 1, the order in which the microparticles and the bone filling material are introduced is merely exemplary, and it is understood that the bone filling material may be introduced first or contemporaneously with the introduction of the microparticles.

At step 16, the bone filling material components and the microparticles may be combined or mixed to form a modulated bone augmentation material in which the microparticles are generally suspended in and dispersed throughout the bone filling material. The microparticles may be added until the concentration of microparticles in the mixture lowers the overall modulus of elasticity of the final cured or hardened modified bone filling material to a level that more closely matches the modulus of the adjacent bone or to a level that at least reduces the risk of damage to the adjacent bone that could otherwise be caused by the unmodulated bone cement. In certain patients, it may be desirable to reduce the modulus of elasticity to a level lower than natural cancellous bone. For example, a modulus of elasticity for hardened bone augmentation material that is less than five times that of cancellous bone may be suitable for some patients. At step 18, the mixture of bone filling material and microparticles may be transferred to a delivery system, such as a syringe or a threaded material dispensing system, and readied for delivery into the target bone region. In alternative embodiments, the bone filling material and the microparticles may be mixed in the same container that will be used to dispense the mixture such that the material transfer of step 18 becomes unnecessary.

Other additives may be added to the bone filling material either during the preparation of the bone filling material or during subsequent mixing with the microparticles. Alternatively, additives may be added to the inner region or to the outer shell material of the microparticles. Where additives are added to the inner region of the microparticles, the outer shell may be porous or at least partially open to allow the additives to pass through the outer shell. Additives that include radiocontrast media may be added to the bone filling material to aid in visualizing the bone augmentation material with imaging equipment. Suitable radiocontrast materials may include barium sulfate, tungsten, tantalum, or titanium. Additives that include osteoconductive or osteoinductive materials may be added to promote bone growth into the hardened bone augmentation material. Suitable osteoconductive materials may include hydroxyapatite (HA), tricalcium phosphate (TCP), HA-TCP, calcium phosphate, calcium sulfate, calcium carbonate, and/or bioactive glasses. Suitable osteoinductive materials may include proteins from transforming growth factor (TGF) beta superfamily, or bone-morphogenic proteins, such as BMP2 or BMP7. Pharmacological agents may be added to promote healing and prevent or fight infection. Suitable pharmacological additives may include antibiotics, anti-inflammatory drugs, or analgesics. As mentioned above, the outer shell of the microparticle may be formed of biodegradable material which may be appropriate for the release of added agents.

At step 20, the modulated bone augmentation material including the microparticles, bone filling materials, and any additives may be delivered into the target bone region in a patient's anatomy. Although the target bone region will often be in a bone, other bone regions, such as joints, may receive the modulated bone filling material to, for example, promote fusion. Examples of target bone regions may be fractured cortical or cancellous bone, osteoporotic cancellous bone, or degenerated intervertebral discs. By matching the modulated bone augmentation material to the material properties of the adjacent bone, complications associated with unaltered, high modulus bone cements may be minimized. In particular, matching the material properties may provide a uniform stress distribution, minimizing significant stress concentrations that may pose a fracture risk to adjacent bone.

Figure 4:
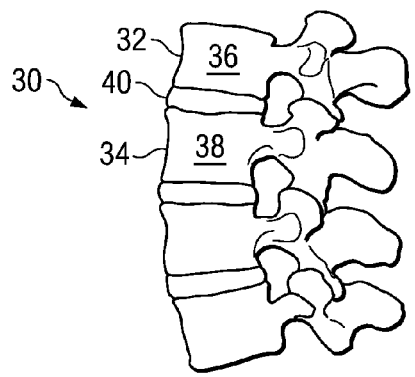
FIG. 4 is a sagittal view of a section of a vertebral column.

Referring now to FIG. 4, in one embodiment, a modulated bone filling material formed by method 10 may be used to augment or replace portions of a vertebral column. The reference numeral 30 refers to a healthy vertebral joint section of a vertebral column. The joint section 30 includes adjacent vertebrae 32, 34 having vertebral bodies 36, 38, respectively. An intervertebral disc 40 extends between the vertebral bodies 36, 38. Although FIG. 4 generally depicts a lumbar region of the spine, it is understood that the systems, materials, and methods of this disclosure may be used in other regions of the vertebral column including the thoracic or cervical regions.

Figure 5:
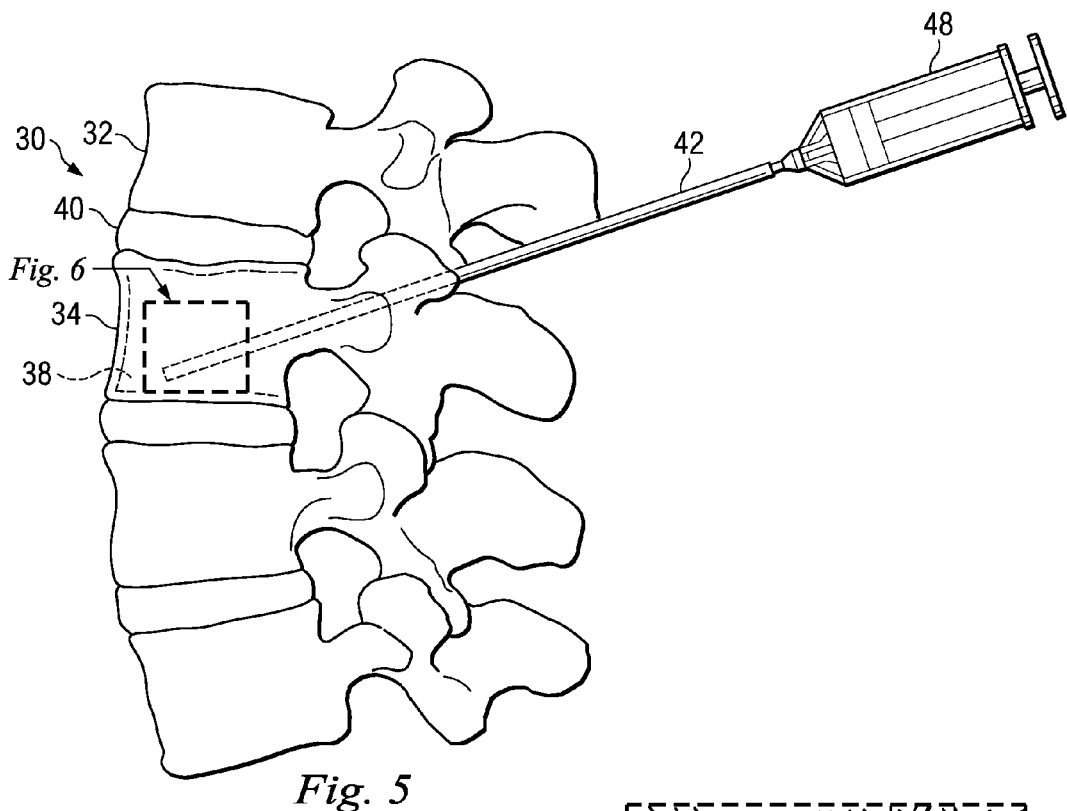
FIG. 5 is a sagittal view of a section of a vertebral column undergoing a vertebroplasty procedure using the modulated bone augmentation material.
Figure 6:
FIGS. 6-7 are a detailed views of the procedure of FIG. 5.
Figure 7:
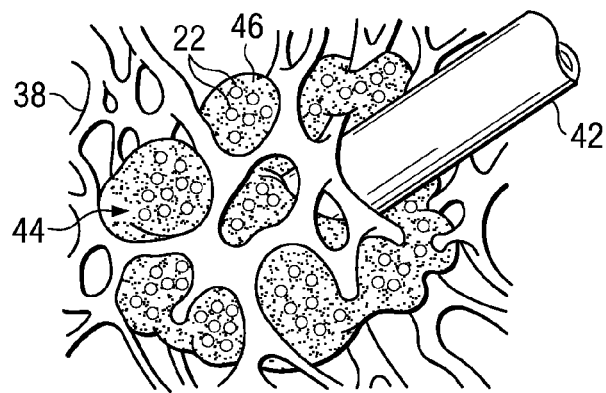
Figure 8:
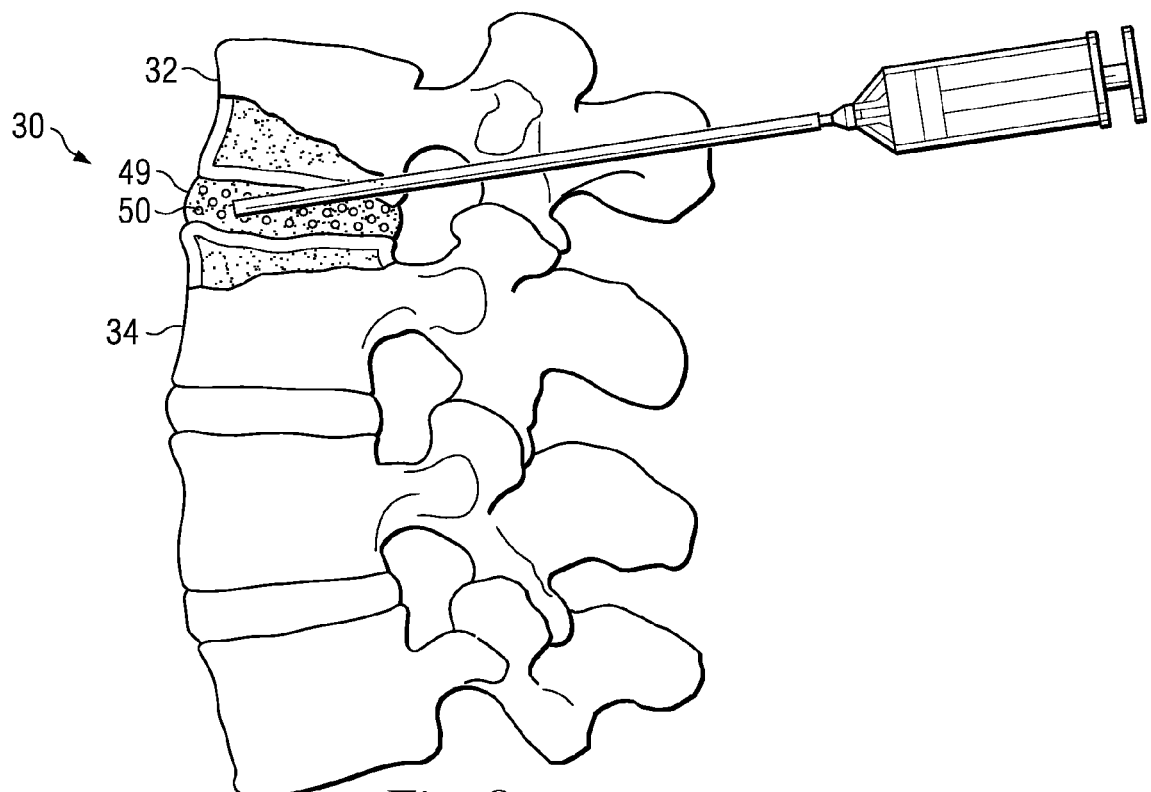
FIG. 8 is a sagittal view of a section of a vertebral column with an intervertebral disc treated with bone filling material and microparticles.

Referring now to FIGS. 5-7, due to traumatic injury, cancer, osteoporosis or other afflictions, the vertebral body portion 38 of the vertebra 34 may begin to collapse, causing pain and loss of bone height. One procedure for restoring the vertebral height, reducing pain, and/or building mass is known as vertebroplasty. In a vertebroplasty procedure according to one embodiment of this disclosure, a stylet or other sharpened instrument (not shown) may be inserted into an injection instrument such as a cannula 42 and arranged so that a sharpened tip protrudes through the end of the cannula. The assembled stylet and cannula 42 may then be inserted through a pedicle of the vertebra 34 and into the cancellous bone of the vertebral body 38. This insertion may be guided through the use of fluoroscopy or other imaging modalities. With the cannula 42 in place in the vertebral body 38, the stylet may be withdrawn, leaving the cannula in place to serve as a pathway for delivering instruments or materials into the bone. In alternative embodiments, a surgical needle having a cannulated body and a pointed tip may be used to access the vertebral body.

Following the method 10, described above, a modulated bone augmentation material mixture 44 comprised of a mixture of bone cement 46 and the microparticles 22 may be formed and transferred to a delivery system 48. The delivery system 48 may be a conventional syringe, having a material reservoir and a plunger mechanism movable therethrough, or a more sophisticated threaded injection system such as the type covered by, for example, U.S. Pat. No. 6,348,055 which is incorporated by reference herein. The delivery system 48 may be actuated, such as by moving the plunger mechanism into the material reservoir, to move the mixture 44 through the cannula 42 and into the vertebra 34 where the mixture may flow into the interstices of the cancellous bone of the vertebral body 38 as shown in FIG. 7. It is understood that the microparticles 22 shown in FIG. 7 are not to scale but rather are merely exemplary of the random disbursement of the microparticles within bone filling material. As described above, within any given mixture of modulated bone augmentation material, the microparticles may have different sizes and/or material properties. Further, the density of microparticles may be determined based upon the degree to which the original bone filling material must be modified to achieve an acceptable modulated bone augmentation material.

With the microparticles 22 distributed throughout the bone cement 46, the modulated bone augmentation mixture 44 may be cured or otherwise allowed to harden within the vertebral body 38. The microparticles 22 may remain suspended in the hardened bone cement 46, reducing the overall stiffness of the modulated bone augmentation material 44. The modulus of elasticity of the hardened modulated bone augmentation material 44 may be lower than that of the hardened bone filling material 46, alone, and closer to the modulus of elasticity of the cancellous bone of the vertebral body 38 than that of the hardened bone filling material alone. Thus, the material 44 may create a more uniform stiffness in the vertebral body 38, avoiding the significant alterations in stress distribution that would be associated with the use of bone cement alone. The more uniform stiffness in the vertebral body 38 may lower the risk for fracture in the adjacent vertebrae.

Although the use of the mixture 44 of microparticles 22 and bone filling material 46 has been described for use in a vertebroplasty procedure, it is understood that in alternative vertebral body treatments, channels or voids may be formed in the vertebral body using probes, balloons, drills, cutting blades or other devices. In these embodiments, the mixture of microparticles and bone filling material may be used to fill the preformed voids or channels. The reduced modulus may be particularly effective in these embodiments as the otherwise unmodulated, large concentrations of bone cement accumulating in the preformed voids would give rise to significant alteration is the stress distribution.

Although the use of microparticles to modulate bone augmentation material has been described primarily for vertebral body applications, it is understood that the same modulated material may be used for other procedures where reduced modulus bone cement may be desirable. For example, the modulated material may be useful for fracture repair.

In one alternative embodiment, a modulated material 49 including microparticles 50 may be created using the method 10 and may be used to fuse the joint section 30. The fusion of the joint 30 may be accomplished using conventional fusion techniques including transforaminal lumbar interbody fusion (TLIF), posterior lumbar interbody fusion (PLIF), or anterior lumbar interbody fusion (ALIF) procedures. Such techniques may involve the use of cages or other intervertebral spacers to maintain the height of the disc space. As a supplement or replacement for the bone graft or bone cement that would otherwise be used in a spinal fusion procedure, the modulated material 49 may be injected into the disc 40 or the disc space remaining after the removal of disc 40. The modulated material 49 may flow into crevices, voids, or prepared areas of the adjacent vertebral endplates. After hardening, the material 49 may have a modulus of elasticity similar to that of the adjacent endplates of the vertebrae 32, 34, or at least lower than unmodulated bone cement. Use of the modulated material 49 may reduce the risk of the hardened material subsiding into the endplates of the adjacent vertebrae 32, 34.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for treating a vertebral bone comprising:
providing a plurality of hollow microparticles wherein the microparticles have an outer shell and an inner region, the outer shell of each microparticle having a braided, or knit configuration;
wherein the outer shell is formed of metal;
providing a flowable and settable bone filling material;
mixing the plurality of hollow microparticles with the bone filling material to form a bone augmentation material;
forming a void in the vertebral bone;
inserting an injection device into the vertebral bone;
injecting the bone augmentation material from the injection device and into the vertebral bone, wherein the microparticles are randomly distributed throughout the bone cement.

2. The method of claim 1 wherein each of the plurality of microparticles is generally spherical.

3. The method of claim 1 wherein the inner region is void of material.

4. The method of claim 1 wherein the inner region is filled with a fluid.

5. The method of claim 1 wherein each of the plurality of microparticles is between 1 and 2000 microns in diameter.

6. The method of claim 1 wherein each of the plurality of microparticles is between 10 and 500 microns in diameter.

7. The method of claim 1 wherein each of the plurality of microparticles is between 25 and 250 microns in diameter.

8. The method of claim 1 wherein the flowable and settable bone filling material comprises polymethylmethacrylate.

9. The method of claim 1 wherein the flowable and settable bone filling material comprises calcium phosphate.

10. The method of claim 1 wherein the flowable and settable bone filling material comprises calcium sulfate.

11. The method of claim 1 wherein the flowable and settable bone filling material comprises hydroxyapatite.

12. The method of claim 1 wherein the bone augmentation material has a lower modulus of elasticity than the bone filling material when hardened.

13. The method of claim 1 further comprising injecting the bone augmentation material from the injection device and into an intervertebral disc space adjacent the vertebral bone.

14. The method of claim 1 wherein the bone augmentation material includes a radiocontrast media.

15. The method of claim 1 wherein the bone augmentation material includes an osteoconductive material.

16. The method of claim 1 wherein the bone augmentation material includes an osteoinductive material.

17. The method of claim 1 wherein the bone augmentation material includes a pharmacological agent.

* * * * *